US005208356A

United States Patent [19]
Pariza et al.

[11] Patent Number: 5,208,356
[45] Date of Patent: May 4, 1993

[54] OCTADECADIENOIC PHOSPHOLIPIC ESTERS, ANTIOXIDANT AND MOLD INHIBITING COMPOSITIONS

[75] Inventors: Michael W. Pariza, Madison, Wis.; Yeong L. Ha, Pusan, Rep. of Korea

[73] Assignee: Wisconsin Alumni Research Foundation, Madison, Wis.

[21] Appl. No.: 679,841

[22] Filed: Apr. 3, 1991

Related U.S. Application Data

[63] Continuation-in-part of Ser. No. 313,120, Feb. 17, 1989.

[51] Int. Cl.$^5$ ............................................. C07F 9/02
[52] U.S. Cl. ........................................ 554/79; 554/78; 554/4; 514/76
[58] Field of Search .............. 260/403; 554/121, 126, 554/224, 79, 78; 518/558

[56] References Cited

PUBLICATIONS

Hunter et al., Journal of Biological Chemistry, vol. 251, #8, pp. 2241–2247, 1976.
Kepler et al., Journal of Biological Chemistry, pp. 5686–5697, 1967.
Chemical Abstracts, vol. 113, #17, p. 819, 1990, 152824m.
Y. L. Ha, N. K. Grimm and M. W. Pariza, in *Carcinogenesis*, vol. 8, No. 12, pp. 1881–1887 (1987).
Y. L. Ha, N. K. Grimm and M. W. Pariza, in *J. Agric. Food Chem.*, vol. 37, No. 1, pp. 75–81 (1987).
T. Osawa and M. Namiki, *Agric. Biol. Chem.*, 45 (3), pp. 735–739 (1981).
M. W. Pariza, Food Research Institute 1988 Annual Fall meeting, Oct. 12, 1988.
*Science News*, vol. 135, No. 6, p. 87 (1989).
Hyoshi et al., *Chemical Abstracts*, 80, 46644t (1974).
Streitwieser, Jr. et al., *Introduction to Organic Chemistry*, Second Edition, pp. 504–505 (1981).
Mahfouz et al., *Biochemica et Biophysica Acta.*, vol. 618, pp. 1–12, 1980.

*Primary Examiner*—José G. Dees
*Assistant Examiner*—Deborah D. Carr
*Attorney, Agent, or Firm*—Quarles & Brady

[57] ABSTRACT

Substantially pure, non-toxic salts and esters of conjugated linoleic acid (CLA) are useful as antioxidants and as mold growth inhibitors. Methods of making the cis-9, trans-11 isomer of linoleic acid and the compounds are also disclosed.

1 Claim, 1 Drawing Sheet

OCTADECADIENOIC PHOSPHOLIPIC ESTERS, ANTIOXIDANT AND MOLD INHIBITING COMPOSITIONS

RELATED CASE

This application is a continuation-in-part of our pending application U.S. Ser. No. 313,120, filed Feb. 17, 1989.

FIELD OF THE INVENTION

The present invention relates generally to methods and compositions for inhibiting mold growth and preventing oxidation. More particularly, it relates to compounds and compositions which can be used to inhibit mold growth and prevent rancidity in natural food products.

BACKGROUND OF THE INVENTION

Among the additives most widely used in food products are the antioxidant compounds butylated hydroxyanisole (BHA) and butylated hydroxytoluene (BHT). Both BHA and BHT are relatively non-toxic; however, they do not inhibit mold growth.

Among the compounds most widely used to prevent mold growth are sorbic acid and its potassium salt. These compounds are relatively non-toxic but they too are not naturally occurring and cannot be used in true "natural" foods.

There is a need for natural, safe and effective methods of preventing mold growth and inhibiting oxidation in food. There also is a need for safe and effective compounds and compositions for use in such methods.

BRIEF SUMMARY OF THE INVENTION

The primary object of the present inventions is to disclose novel, substantially pure, compounds and compositions which are especially useful in methods of inhibiting mold growth and preventing oxidation.

It is a further object to disclose simple methods of preparing such compounds and compositions.

The novel compounds of the present invention are the substantially pure, water soluble salts of the conjugated linoleic acids (CLA), 9,11-octadecadienoic acid and 10,12-octadecadienoic acid, and the esters of CLA and the cis-9, trans-11 isomer. The compositions of the present invention are compositions containing those compounds.

The novel, water soluble, non-toxic compounds and the novel non-toxic esters of the present invention are prepared in substantially pure form by conventional methods from a mixture of the free acid forms of CLA or the cis-9, trans-11 isomer. For example, the non-toxic salts can be made by simply reacting the free acids with a non-toxic base.

A mixture of the free acid forms of the CLA can be prepared by reacting linoleic acid with a protein, such as whey protein, which is capable of effecting the transformation of linoleic acid to CLA at temperatures up to about 85° C. and then isolating the CLA.

The free acid form of the cis-9, trans-11 isomer, which is believed to be the biologically active form of CLA, can be prepared by treating a food grade oil, such as safflower oil, hydrolysate containing linoleic acid with a linoleate isomerase at ambient temperatures and then isolating the desired product. A suitable linoleate isomerase is that extracted from the harmless rumen bacterium, *Butyrivibrio fibrosolvens*, as described by Kepler et al. in the Journal of Biological Chemistry, Vol. 242, pp. 5686–5692 (1967).

The novel substantially pure esters of the present invention are either prepared by conventional esterification procedure from the free acids or extracted in substantially pure forms from biological sources.

The novel compositions of the present invention are those compositions which contain a substantially pure form of either a novel water soluble salt or an ester of either CLA or the cis-9, trans-11 isomer.

In the preferred methods of inhibiting oxidation or preventing mold growth, a safe and effective amount of one or more of the compounds or compositions of the present invention are either added to a product or generated in situ in the product.

Description of the Preferred Embodiments

Figure 1:
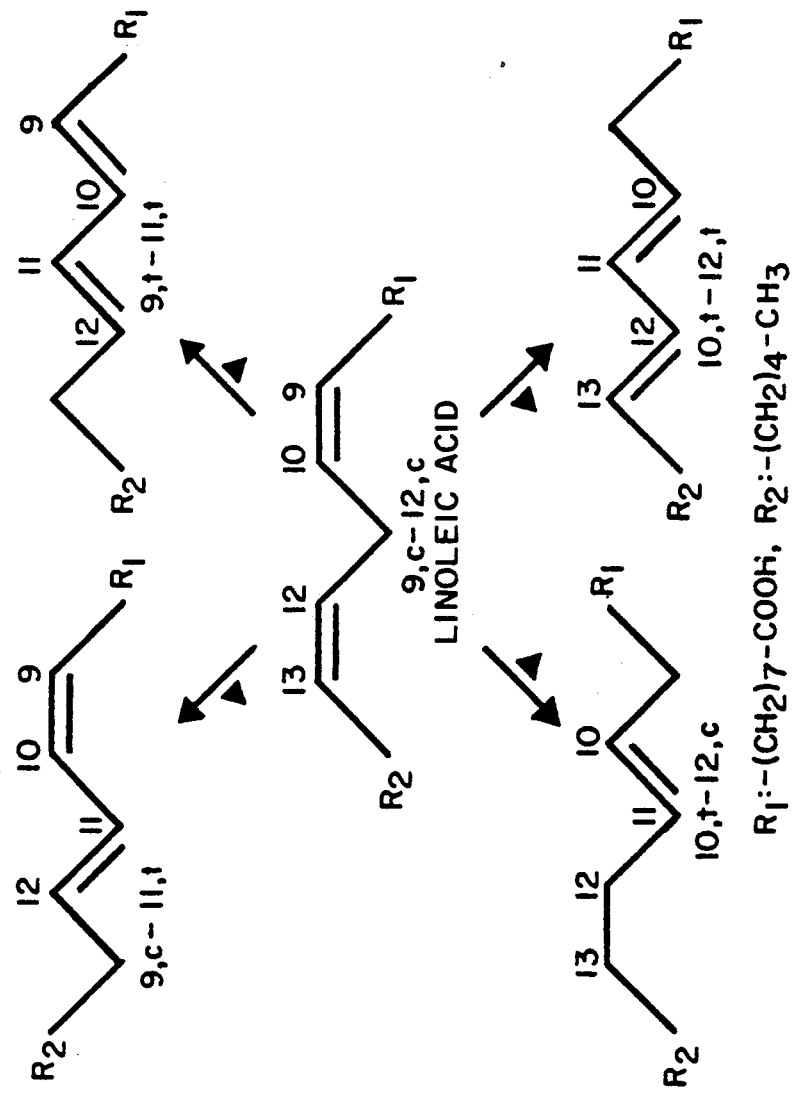
FIG. 1 shows a model for the formation of CLA from linoleic acid.

The non-toxic water soluble salts of the CLA mixture or the cis-9, trans-11 isomer can be readily prepared by reacting chemically equivalent amounts of a source of the CLA mixture or the isomer with a suitable base, such as sodium or potassium hydroxide, at a pH of about 8 to 9.

Representative of the water soluble salts which can be used to prevent oxidation or inhibit mold growth are the following:
Sodium CLA
Potassium CLA
The sodium salt of the cis-9, trans-11 isomer
The potassium salt of the cis-9, trans-11 isomer.

The CLA mixture may be prepared in small amounts by reacting roughly equivalent amounts of a natural source containing linoleic acid, such as butter fat, with milk whey protein at ambient temperatures. The reaction proceeds quickly even when the ingredients are simply intimately mixed. The CLA obtained by the practice of this method contains a mixture of one or more of the 9,11-octadecadienoic acids and/or 10,12-octadecadienoic acids and active isomers thereof.

The preferred protein which is used to transform linoleic acid to CLA is whey protein which contains sulfhydryl groups and is, of course, readily available. Other proteins that will transform linoleic acid to CLA can be readily determined without undue experimentation by those skilled in the art. Among such proteins would be those that contain sulfhydryl groups, as well as, non-sulfhydryl containing proteins.

The chemical synthesis of CLA from linoleic acid is possible; however, it involves the use of toxic chemicals such as ethylene glycol. In addition, synthetically prepared CLA contains several isomers. Of the individual isomers c-9, t-11 and t-10, c-12 usually accounted for 45% and 50% of the mixture, respectively. Thus, CLA synthesized from natural methods is preferred.

The biologically active cis-9, trans-11 isomer can be conveniently prepared by reacting either a linoleic acid containing hydrolysate or the free linoleic acid with a suitable linoleate isomerase, as previously described. The linoleate isomerase isolated from the rumen bacteria, *Butyrivibrio fibrisolvens* is preferred.

The method of preparation employing a linoleate isomerase requires free linoleic acid; it does not appear that triglycerides containing linoleic acid will work.

However, a hydrolysate of a food grade oil, such as safflower oil, can be used as an economical source of linoleic acid. The hydrolysate can be produced chemically or with a lipase.

The cis-9, trans-11 isomer can also be produced in situ in a food product by adding the enzyme and a linoleic acid source to the food product.

The simple esters of CLA and the cis-9, trans-11 isomer can be prepared by conventional esterification techniques. The more complex esters of CLA, such as the phospholipid esters, can be made using suitable enzymes or in the case of the phospholipid ester by feeding an animal the cis-9, trans-11 isomer for a suitable length of time, sacrificing the animal and extracting the naturally formed phospholid ester in a sustantially pure form.

Representative of the esters of the present invention are the following:
  CLA methyl ester
  Triglyceride esters of CLA and the cis-9, trans-11 isomer
  Phospholipid ester of the cis-9, trans-11 isomer.

The compounds can be added to products per se or combined with other ingredients to form compositions to inhibit oxidation mediated by free radicals or by singlet oxygen. The amounts of the compounds to be employed are roughly equivalent to the amounts of BHA or BHT that are now being used. The exact amount to be added, of course, depends upon the compound employed, the nature of the product, the packaging, and the conditions of storage and use. Generally, the amount employed of the active compound(s) will range from about one part per million (ppm) to about 1,000 ppm of product.

When used for mold growth inhibition, a water soluble compound or composition is preferably added to the product to be protected in safe and effective amounts. The exact amount to be employed will, of course, depend upon the compound or composition employed, the packaging and the conditions of storage and use. Generally, the amount employed of the active substance will range from about 1,000 ppm to about 10,000 ppm per gram of product. The water soluble compounds and compositions, especially the non-toxic salts, appear to be as effective as sorbic acid or potassium sorbate at similar concentrations. The ester form of the CLA can also be effective for mold inhibition, especially where the chelation of metals, such as iron, plays a role in the mold inhibition mechanism.

The exact mechanisms by which the compounds and compositions of the present invention act as antioxidants or to quench singlet oxygen are not known. However, it is believed that they somehow tie up and defuse free radicals and singlet oxygen. A possible mechanism of action for CLA as an antioxidant is based on the report of Osawa and Namiki (Agric. Biol. Chem. 45: 735–739, 1981). In that report novel diketone with antioxidant activity was isolated from Eucalyptus leaves and was determined chemically to be n-tritriacontan-16, 18-dione. It is proposed that a similar novel diketone with antioxidant activity may form when CLA is exposed to oxygen. The diketone would result from the reaction of molecular oxygen and activated oxygen species with the conjugated double bond system of CLA. The mechanism by which the water soluble derivatives of CLA inhibit mold and yeast growth is not known.

The following examples further illustrate the present invention.

EXAMPLE 1

Preparation of CLA

Forty grams of whey protein and forty five grams of a fat source containing linoleic acid (butter fat) were intimately mixed at ambient temperature and then pasteurized at 85° C. for 5 minutes. After 30 minutes the mixture was assayed for CLA as previously described. The CLA thus formed was stable at 25° C. for up to 8 weeks.

EXAMPLE 2

Preparation of cis-9,trans-11 Isomer

*Butyrivibrio fibrisolvens* was grown under anaerobic conditions for 16–18 hr at 37 C and was harvested by centrifugation (3000×g for 5 min). The residual material was scraped out of centrifuge tubes and resuspended in 0.1 M of phosphate buffer pH 7.0 (2 ml buffer for each liter of starting media). The material was dispersed by shaking with glass beads and then filtered through two layers of cheese-cloth. Cells were disrupted by means of a French pressure cell at 17,000 psi and centrifuged at 10,000 for 20 min. The solid material was discarded and the supernatant was centrifuged for 34,000×g for 30 min, decanted, and recentrifuged at 34,000×g for 30 min. The supernatant solution from the last centrifuge was then centrifuged at 133,000×g for 3 hr. The supernatant was discarded and each pellet was rinsed with 2 ml of phosphate buffer. Pellets were pooled and resuspended in 0.1 M phosphate buffer pH 7.0 (1 ml for each liter starting media). The enzyme mixture was then dispersed by sonic oscillation for 30 sec and subdivided into freezing vials, gassed with nitrogen and stored at −20° C.

A fresh stock substrate solution of hydrolyzed safflower oil or linoleic acid in 1,3-propanediol was prepared by a 1-min exposure to sonic oscillation. Substrate solution (0.1 ml) was mixed with 2.7 ml of 0.1 M potassium phosphate buffer (pH 7.0) and 0.2 ml of 1,3-propanediol. The substrate buffer mixture was preincubated in a water bath at 35° C. for 5 min prior to the initiation of the reaction with 0.1 ml of enzyme. The reaction was terminated after 30 min of incubation.

The product from the incubation was extracted with chloroform: methanol (2:1) and methylated with 2% sulfuric acid in methanol. Analysis of the total CLA and c-9, t-11 isomer were carried out on HPLC and GC, respectively.

EXAMPLE 3

Preparation of Potassium Salt of CLA

The potassium salt of CLA was prepared by adding about 50 g. of CLA to 100 ml of water, adjusting to pH 8.5 with 1N KOH, and freeze drying. The resulting product was a white powder.

EXAMPLE 4

Preparation of Sodium Salt of CLA

The sodium salt of CLA was prepared by adding about 50 g. of CLA to 100 ml of water, adjusting to pH 8.5 with 1N NaOH, and freeze drying. The resulting product was a white powder.

EXAMPLE 5

Prevention of Oxidation 0.1 mg of CLA prepared by alkali-isomerization of linoleic acid was added to 100 mg of linoleic acid in a reaction medium containing 10 ml of phosphate buffer (pH 8.0, 0.2M); 10.5 ml ethanol and 4.5 ml water. The resulting composition was incubated at 40° C. for up to 15 days. The peroxide produced was measured by the thiocyanate method in which peroxide oxidizes $Fe^{++}$ to $Fe^{+++}$ in the presence of cyanate to give a color exhibiting maximum absorption at 480 nm. The results obtained were equivalent to those obtained with similar amounts of BHA and better than other antioxidants (See FIG. 3).

EXAMPLE 6

Inhibition of Mold Growth

The addition of 1% potassium CLA to YM agar medium inhibited mold growth better than 1% potassium sorbate in the same medium under the same conditions.

EXAMPLE 7

Singlet Oxygen Quenching

The reaction medium contained (per 5 ml of acetonitrile solvent):
Linoleic Acid (LA): LA (0.007M)+rose bengal ($0.5 \times 10^{-4}$M).
CLA: CLA (0.007M)+rose bengal ($0.5 \times 10^{-4}$M).
LA+CLA: LA (0.007M)+CLA (0.007M)+rose bengal ($0.5 \times 10^{-4}$M). The sample was illuminated by a tungsten lamp (60 w, 13 cm distance) for various times. The peroxide produced was measured by iodometric method (peroxide oxidize iodine anion ($I^{-1}$) to iodate ($I_2$) to give yellow color exhibiting max absorption at 350 nm.

Materials and Methods

Materials. Organic solvents (HPLC grade; Burdick and Jackson Chemical Co., Muskegon, Mich.); 12-hydroxy-c9-octadecenoic acid (ricinoleic acid, 99%), 12-hydroxy-t9-octadecenoic acid (ricinelaidic acid, 99%), c9, c12-octadecadienoic acid (linoleic acid, 99%) and other fatty acid standards (Sigma Chemical Company, St. Louis, Mo.); and trifluoroacetic anhydride, R-(−)-2-phenylbutyric acid (PBA) and 4-phenyl-1,2,4-triazoline-3,5-dione (PTAD) (Aldrich Chemical Co., Milwaukee, Wisc.) were used. A 1.0 mg PBA/0.1 ml concentration was prepared with a 2:1 chloroform:methanol (v/v) mixture. Alkali-isomerized linoleic acid was prepared according to the method as previously described (Ha et al., 1987). Cheese and ground beef samples were purchased from the Department of Food Science, University of Wisconsin-Madison (Table I).

Preparation of CLA isomer standards. The methyl ester of t10,c12-octadecadienoate was prepared by crystallization from methyl esters of alkali-isomerized linoleic acid. Methyl t10,t12- and c10,c12-octadecadienoate were prepared from the t10,c12-isomer by iodine and light isomerization. The prepared 10,12-isomers were purified by the normal-phase semi-preparatory HPLC as described below in the HPLC section. A typical semi-preparatory normal-phase HPLC profile of the methyl t10,c12-octadecadienoate prepared exhibited 3 components (peaks 1, 40.1 min; 2, 47.5 min; and 3, 65.1 min), which were present in relative proportions of 89, 2 and 9%, respectively. Subsequent capillary GC analyses, using conditions described in the GC section, of these peaks revealed that peak 1 is a methyl t10,c12-isomer of greater than 95% purity, while peaks 2 and 3 are unknown impurities. The remaining 10,12-geometrical CLA standards were similarly purified by this HPLC procedure.

The 9,11-octadecadienoic acid isomers (c,c; c,t; and t,t) were prepared from ricinoleic acid or ricinelaidic acid, and the individual isomers were separated by the argentation HPLC method.

Preparation of free CLA. This procedure includes extraction and saponification of CLA. Sample material (1 g) containing 1.0 mg PBA (internal standard) was homogenized with 20 ml of 2:1 chloroform:methanol (v/v) for 60 sec in a Polytron homogenizer (Brinkman instruments, Westbury, N.Y.) at medium speed. Another 10 ml of the chloroform:methanol mixture was used to rinse the Polytron probe and combined with the homogenate, followed by addition of 10 ml double distilled water. For milk, 5 g sample, 5.0 mg PBA and 150 ml of chloroform:methanol mixture were used. The homogenate was centrifuged at 2,000 rpm for 30 min (4° C.). The organic layer was separated, dried over $Na_2SO_4$ anhydrous, and roto-evaporated. Total fat content was determined from the residue. Free fatty acids were prepared by heating the fat extracts in 2 ml of 1.0 N-sodium hydroxide in methanol (v/v) in a screw-capped test tube (15×1.5 cm). After being heated in a boiling water bath for 15 min the solution was acidified to pH 1 with 5.5 N-sulfuric acid in water (v/v). The free fatty acids were extracted using 3×10 ml portions of heptane. The organic extract was washed with water, dried over $Na_2SO_4$ anhydrous and the filtered solvent was removed under vacuum with a rotary evaporator.

The effect of this procedure on CLA formation was investigated. When linoleic acid (2.0 mg) was subjected to the procedure, no CLA was detected as determined by UV absorbence at 235 nm using a Beckman DU-50 Spectrophotometer and by the semi-preparatory reversed-phase HPLC as described below. This finding indicates that CLA was not formed as a result of extraction/saponification by our methods.

HPLC separation. Separation and purification of CLA by HPLC were performed at room temperature using a Beckman Model 421A microcontroller system fitted with two solvent delivery modules (Beckman model 110A) and a dual channel UV detector (Micromeritics 788 model; Norcross, Ga.). Eluent was monitored at 235 or 245 nm. Peak areas were recorded with a Spectra Physics 4270 integrator. CLA in the sample was separated on a semi-preparatory reversed-phase column (Ultrasphere-ODS, 5 μm, 250×10 mm, i.d., Beckman) with a gradient mobile phase (acetonitrile and water) as previously reported (Ha et al., supra). The purification of individual isomers or alkali-isomerized linoleic acid was performed on a normal-phase semi-preparatory column (Ultrasil-$NH_2$, 5 μm, 250 mm×10 mm, i.d., Beckman) using a gradient system. The starting mobile phase (99:1 hexane:ethanol, v/v) and flow rate (1.0 ml/min) were maintained for 20 min and then both hexane proportion and flow rate were linearly increased to 100% and 4.0 ml/min, respectively,, over 20 min.

These conditions were held for an additional 40 min and then returned to the starting conditions for 10 min. The system was reequilibrated at least 10 min prior to the next injection.

Preparation of CLA derivatives. CLA methyl esters were prepared from the free acid form using boron trifluoridemethanol according to the AOCS method Ce2-66 (1973). The PTAD derivative of CLA methyl ester was prepared according [to the method of Young, et al., Anal. Chem (1987) 59, 1954–1957 after methylation of CLA.

GC analysis. GC analysis of CLA methyl ester or CLA methyl ester derivatized with PTAD was carried out with a Varian 3700 gas chromatograph fitted with a flame ionization detector (FID) and a Spectra Physics 4270 integrator. The column used was a Supercowax-10 fused silica capillary column (Supelco Inc.): 60 m × 0.32 mm, i.d. with a 0.25 μm film thickness. GC conditions consisted of an on-column injection system with helium as the carrier gas at 2 ml/min linear gas flow rate. Temperatures were programmed as follows: oven, 50–200° C. at 20° C./min and held for 60 min; and injector, 50–200° C. at 100° C./min after injection. Detector temperature was 250° C. The volume injected ranged from 1.0 to 2.0 μl, containing 0.5 to 5.0 μg CLA/μl.

GC-MS analysis. GC-MS analysis was conducted with a Finnigan 4510 GC-EI/CI automated mass spectrometer system using a splitless injector and a Supercowax-10 capillary column (60 m × 0.32 mm, i.d., 2.5 μm film thickness). The column temperature was programmed as specified in the GC analysis section. Electronic impact (EI) ionization and chemical ionization (CI) were carried out at 70 ev and 100° C. as a source temperature. The CI spectrum was obtained using isobutane as a reagent gas. For the analysis of PTAD derivatives of CLA methyl esters, a DB-5 glass capillary column (30 m × 0.32 mm, i.d., 1.0 um film thickness) was used with a temperature program; 60°–250° C. at 10° C./min after one min holding at 60° C. The data were analyzed by a Data General NOVA/4 system equipped with a CDC-CMD disk driver.

GC-FT/IR analysis. GC-FT/IR analysis was performed with a Nicolet model 60S FT/IR using a Supercowax-10 capillary column (60 m × 0.32 mm, i.d., 0.25 μm film thickness). GC conditions were the same as those for GC analysis.

CLA quantification. Quantification of individual CLA isomers in a sample was based on the internal standard method. To obtain correction factors (CF) for individual CLA isomers, a reference mixture consisting of known amounts of the isomers plus PBA was subjected to the extraction procedure and reversed-phase HPLC analysis. Pooled CLA and PBA peaks from the HPLC were chromatographed on a capillary GC column (Supercowax-10) after methylation. The CF for the individual isomers was calculated as follows: $CF = (Area_{IS}/Weight_{IS}) \times (Weight_x/Area_x)$, IS refers to internal standard and the subscript x refers to a given CLA isomer. Using the $CF_x$, the amount of each CLA isomer in the sample was calculated by the following equation: $ppm_x = [(Area_x/Area_{IS}) \times Weight (mg)_{IS}/sample (gm)] \times CF_x \times 1000$.

Results

GC/HPLC separation. A reversed-phase semi-preparatory HPLC of the sample effected separation of CLA from the other saturated or unsaturated fatty acids. Subsequent GC analysis of the methylated CLA peak indicated that 7 components (peaks 1 through 7) eluted after linoleic acid; these peaks exhibited identical retention times to those of the methylated alkali-isomerized linoleic acid components. Two approaches were employed to identify the isomers: 1) determination of ECL values of CLA isomers; and 2) spectral analyses of the CLA sample or alkali-isomerized linoleic acid containing unidentified peaks for which standards are not available or are difficult to obtain.

Determination of ECL. A chromatogram showed that the GC profile (Supercowax-10) of the methyl esters of saturated fatty acid standards (C16:0, C17:0, C18:0, C20:0 and C22:0) plus that of a methylated CLA sample. ECL values of CLA methyl ester isomers were determined by plotting carbon numbers vs retention times on semilog paper. The ECL values of CLA methyl esters ranged from 19.49 for peak 1 to 20.01 for peak 7. The ECL values and elution orders have been reported for some of the geometrical/positional isomers of CLA methyl esters separated on a 100-m glass capillary Silar 10C column. The difference in ECL (Delta ECL) remained constant within 0.01–0.03 unit for the isomers tested by both columns. The correlation coefficient (r value) was 0.9995 for the available standards on the two columns. The column (Supercowax-10) that we used is only slightly less polar than a Silar 10C column. Therefore, the ECL data are comparable.

A CLA methyl ester standard was co-chromatographed with a methylated CLA sample containing unidentified peaks. For those peaks that co-chromatographed with a standard CLA methyl ester, identity is set as such. This relationship was then used to determine the identities of the remaining unknown peaks.

According to the ECL relationship and co-chromatographic results, peaks 1, 3, 5, 6 and 7 were identified as methylesters of c9, t11- and/or t9, c11-, t10, c12-, c9, c11-, c10,c12- and t9,t11- and/or t10,t12-octadecadienoates, respectively.

Identification of peaks 2 and 4. The methyl esters of alkali-isomerized linoleic acid or sample CLA were subjected to GC-MS and GC-FT/IR analyses. EI-MS data of peaks 2 and 4 were identical, yielding fragment (M/e) 67 (base peak), 294 (M+), 74, 59 and 262; hence, these isomers could not be distinguished by this method.

Since under normal EI ionization conditions double bonds can migrate prior to fragmentation making it difficult to determine their original positions, others have used CI-MS to identify the double bond position in hydrocarbon chains and fatty acids. CI-MS data of CLA methyl esters of peaks 2 and 4 exhibited a molecular weight of 294 (M+ +1: 295, 100%). Typical M/e for peak 2 were 113 (3%), 213 (5%), 139 (1%) and 239 (12%), and for peak 4 were 99 (5%), 227 (8%), 125 (1%) and 253 (13%). Cleavage between carbons 10 and 11, and 12 and 13 double bond numbered from carboxyl group yielded M/e 113 and 213, respectively. Cleavage between 8–9 and 14–15 single bond carbons produced M/e 139 and 239, respectively. Hence, peak 2 is identified as a 10,12-positional isomer of methyl octadecadienoate. Peak 4 had M/e 99 derived from cleavage of the double bond between carbons 11 and 12, M/e 227 from cleavage of the double bond between carbons 13 and 14, M/e 125 derived from single bond cleavage between carbons 9 and 10, and M/e 253 from single bond cleavage between carbons 15 and 16, indicating that this compound is an 11,13-positional isomer. Additionally, peaks 1 and 5 contained M/e 127, 199, 153 and 225, indicating 9,11-isomers. Similarly, peaks 3 and 6 contained M/e 113, 139, 213 and 239 and were identified as 10, 12-isomers. Peak 7 contained M/e of both 9,11- and 10,12-isomers. The CLA sample (methyl esters) derivatized with PTAD was chromatographed on a Supercowax-10 column. All peaks of CLA methyl esters disappeared from the GC profile compared with those of underivatized CLA methyl esters. Since PTAD is electrophilic and therefore only reacts with a conjugated double-bond system in hydrocarbon chains or fatty acids via Diels-Alder reaction, peaks 1 through 7 were identified as CLA positional isomers. The PTAD derivatives of CLA methyl esters (molecular weight of 467) that had relatively high polarity were not eluted under these conditions. The Supercowax-10 (polar) column was changed to a DB-5 (non-polar) column to elute the derivatives. A different elution pattern was obtained from that observed with the former column. This method will not identify positional isomers, but it confirms the presence of the conjugated double-bond in the sample and also indicates the location of CLA methyl esters in the GC chromatogram from the Supercowax-10 column. The major differences in GC-FT/IR spectra of peaks 2 and 4 were at the 1000−800 cm$^{-1}$ range. Sharp absorption at 990 and 945 cm$^{-1}$ (peak 2) and broad absorption at 990 cm$^{-1}$ (peak 4) were observed, indicating that peak 2 is a cis, trans-isomer and peak 4 a cis,cis-isomer.

Based on the results of spectral analyses, co-chromatography and ECL values, peaks 1 through 7 were identified as methyl esters of c9,t11- and/or t9,c11-, c10,t12-, t10,c12-, c11,c13-, c9,c11-, c10,c12- and t9,t11- and/or t10,t12-octadecadienoates, respectively.

Application. The newly developed GC/HPLC method to analyze individual CLA isomers was applied to the dairy products and beef. A CLA sample containing PBA was purified on the semipreparatory reversed-phase column. PBA was eluted at 6.2 min and CLA at 40 min. The two pooled peaks were dried over Na$_2$SO$_4$ anhydrous and the organic solvent was evaporated under nitrogen. After methylation of the residue, it was analyzed by GC. PBA was co-eluted with some impurities on the HPLC column, but these impurities did not interfere with CLA isomer resolutions on the GC column.

Quantification of peaks 2 (c10,t12-isomer) and 4 (c11,c13-isomer) was based on an assumption that CF values of these isomers are equal to the average CF values of the remaining five CLA isomers: 0.17, c9,t11-isomer (peak 1); 0.16, t10,c12-isomer (peak 3); 0.17, c9,c11-isomer (peak 5); 0.16, c10,c12-isomer (peak 6); and 0.17, t9,t11- or t10,t12-isomer (peak 7). Total CLA content among cheeses ranged from 169.3 ppm (Blue cheese) to 1815 ppm (CHEESE WHIZ ®). Of the aged natural cheeses, Parmesan cheese aged more than 10 months contained the highest (622.3 ppm) and Blue cheese aged over 100 days contained the lowest amounts of CLA (169.3 ppm), suggesting a positive relationship between the aging period and CLA content. In general, processed cheese contained more CLA than natural cheese. It is interesting to note that raw and pasteurized whole milk both contained similar amounts of CLA. Grilled ground beef contained 994 ppm of total CLA, while uncooked ground beef contained 561.7 ppm. Fat content ranged from 4.0% (pasteurized whole milk) to 35.5% (cream cheese). Based on total fat, the CLA content ranged from 549.8 ppm (Blue cheese) to 9289.7 ppm (grilled ground beef).

Of the individual isomers, t9,t11-/t10,t12-, c9, t11-t9, c11- and t10,c12-octadecadienoic acids accounted for more than 89% of the total CLA in all measured samples. The t,t-isomers ranged from 49.8% (uncooked ground beef) to 78.1% (cream cheese); however, in milk samples approximately 15% of the CLA was present as t,t-isomers. The remaining CLA isomers (c9,c11-, c10,c12-, c10,t12-, c11,c13) contributed less than 11% of the total CLA in the samples.

Origin of CLA. The origin of CLA in cheese and ground beef is not known. CLA formation may be attributed to 1) free-radical type oxidation of linoleic acid effected by aging, heat treatment and protein quality; and 2) isomerization of linoleic and linoleic acids in the rumen.

Aging processes modify the physio-chemical properties of cheese or beef to give typical characteristics. Examples include the oxidation of fats. Under anaerobic conditions this may occur during heating, where oxidation of linoleic acid in glycerides or phospholipids may be initiated to form an allyl radical. The radical would be stabilized through the formation of its resonance forms which require hydrogens to form a conjugated double-bond system. The hydrogens are attributed to proteins which, in turn, form protein radicals. These radicals may be neutralized by alpha-tocopherol in the lipophilic regions. It is known that when linoleic acid was oxidized by UV irradiation in the presence of albumin, 9, 11-conjugated linoleic acid is formed rather than oxidation products, suggesting the importance of protein as a hydrogen source. The importance of protein in CLA formation is also supported by our finding that lactalbumin- and lactoglobulin-enriched cheese contained significantly higher amounts of CLA than other cheeses that were not enriched. CHEESE WHIZ ®, which is enriched with whey concentrate (Table I), contained twice as much CLA as the other processed cheeses. Whey protein contains relatively high levels of lactalbumin and lactoglobulin that could provide a hydrogen source.

CLA isomers that were isomerized from linoleic and linoleic acids in the rumen may contribute directly to the CLA content in cheese or meat. A significant amount of CLA was present in raw whole milk and pasteurized whole milk. A positive correlation has been observed between conjugated dienoic C18 fatty acids of milk with trans isomers and linoleic acid in the diet. These conjugated dienoic fatty acids are also present in butter (1–4.5%) and are directly related to the linoleic acid content in the diet of cows. During biohydrogenation of linoleic or linoleic acid by microorganisms in the rumen, cis-double bonds undergo an extensive isomerization. This may involve a shift in position along with the carbon chain (positional isomerization) or a change of geometrical configuration or both. Isomerization would be the rate controlling step and would determine the final concentration of CLA. In milk or ruminant animal tissues, the isomer ratio is effected by the microbial population in the rumen which, in turn, is influenced by the amount of linoleic acid and/or linoleic acid fed.

Formation of positional/geometrical isomers. The t9,t11- and t10,t12-isomers, and the c9,t11- and t9,c11-isomers could not be separately quantified in this study. However, if we assume that each of the t,t-isomers contributes equally to the total amount of peak 7, and that the total concentration of the t9,c11-isomer co-eluted with c9,t11-isomer in peak 1 is equal to the concentration of the c10,t12-isomer of peak 2, then the following conclusion may be drawn: 1), the molar concentration of the 9,11-positional isomer is identical to the molar concentration of the 10,12-positional isomer; 2), the concentrations of c9,t11-and t11,c12-isomers are equal; 3), there are four major isomers (t9,t11-, c9,t11-, t10,t12- and t10,c12-) and five minor isomers (c9,c11- t9,c11-, c10,c12-, c10,t12- and c11,c13-); and 4), there is a relatively higher concentration (61–78.1% of total CLA in cheese) of t,t-isomers. These conclusions might be explained by the isomerization of linoleic acid and/or linoleic acid geometrical isomers (c9-t12-, t9,t12- and t9,c12-isomers).

Linoleic acid radical containing an unpaired electron on the methylene interrupted carbon (carbon number 11) would stabilize to form resonances via a proton shift. The shift occurs in either the carboxyl group or hydrocarbon terminal direction to make a conjugated double-bond. The probability of the formation of 9,11- or 10,12-isomer is equal due to the distance of the carboxyl group from the double-bond system and/or to the esterfied carboxyl group in the glycerides or phospholipids.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid in the sample apparently resulted from the further stabilization of c9,t11- or t10,c12-geometric isomers, which is thermodynamically preferred, during an extended processing time or long aging period. Additionally the t,t-isomer of 9,11- or 10,12-octa-decadienoic acid that was predominantly formed during the isomerization of linoleic acid geometrical isomers (t9,t12-, c9,t12- and t9,c12-octadecadienoic acid) may influence the final ratio of the isomers or the final CLA content in the samples. These linoleic acid geometrical isomers accounted for up to 11% of the milk fat and for 13.6% of the linoleic acid content in beef. In the case of milk, we observed only 15% of the total CLA content was the t,t-isomers far lower than for the other samples. The reason for this may be that rumen microorganisms preferentially isomerized c9,c12-octa-decadienoic acid to c9,t11-octadecadienoic acid. Subsequent pasteurization of the milk was not sufficient to effect the stabilization of c,t-isomers to the t,t-isomeric forms.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The methods combining reverse-phase HPLC with GC may be used to determine CLA and its isomeric forms in food products. Such information should be of interest given the anticarcinogenic properties of CLA under certain conditions in animal experiments, the fact that CLA has been isolated from human milk, serum, bile and duodenal juice and our discovery that it is an effective antioxidant and mold growth inhibitor.

TABLE I

| Sample | Products studied Descriptive Characteristics |
|---|---|
| 1. Parmesan cheese (Grated) | Part-skim milk, cheese culture, enzymes, aged over 10 months |
| 2. Cheddar cheese (American) | Whole milk, cheese culture enzymes, aged over 6 months |
| 3. Romano cheese (Grated) | Part-skim cow milk, cheese culture, enzymes, aged over 5 months |
| 4. Blue cheese | Whole milk, cheese culture, enzymes, aged over 100 days |
| 5. Past. proc. cheese (American) | American cheese, milkfat |
| 6. Cream cheese | Pasteurized milk, cream cheese culture |
| 7. Cheese spread (Roka blue) | Pasteurized milk, milkfat, cream cheese |
| 8. Cheese Whiz ® (Kraft) | Cheddar cheese, low moisture part-skim Mozzarella cheese whey concentrate |
| 9. Milk Pasteurized whole Non-pasteurized whole | Cow's milk Cow's milk |
| 10. Ground beef | uncooked or grilled |

CLA is naturally present in cheese but is esterified in triglycerides. To be effective in inhibiting mold growth, a water soluble derivative, such as salt form of CLA, must be present.

The antioxidant activity of CLA appears to be greatly enhanced when the CLA is incorporated into a phospholipid. This can be done by feeding CLA or the cis-9, trans-11 isomer to mice, and following sacrifice extracting the liver membrane fraction (microsomes). The microsomes are then subjected to oxidation using a system involving the addition of ascorbic acid and varying levels of iron. Microsomes from such mice are substantially more resistant to oxidation than microsomes from control animals. Furthermore when control microsomes are mixed with increasing amounts of CLA-containing microsomes and a protective effect is observed, that is, the CLA-phospholipid containing microsomes protect the control microsomes against oxidation.

Finally, we determined the amount of CLA in the CLA-containing microsomes. We then added an equivalent amount of potassium or sodium CLA to control microsomes. The result: virtually no protection (much higher levels of the CLA salts would have been required).

The CLA in the microsomes is bound through ester linkages to phospholipid and triglycerides. However, the phospholipid form appears to interact more with water and for that reason, CLA-phospholipid may be of greater practical significance. The results strongly suggest that CLA esterified in phospholipid is more effective as an antioxidant.

The CLA can be introduced into phospholipid enzymatically, such as by using phosphosynthatases, or the cis-9, trans-11 isomer or CLA could be fed for a few weeks to an animal (for example, a chicken) and the "natural" phospholipid containing incorporating CLA extracted in substantially pure form after sacrifice. Biochemical synthesis could also be used to simply mimic the natural process.

The water soluble, non-toxic salts of CLA are the preferred products for inhibiting mold growth. However, for convenience or other reasons, it may be desirable to add the water soluble salts to a product in the form of a solid or liquid composition containing other ingredients, such as diluents, solubilizing agents, emulsifying agents, pigments and the like.

The term "substantially pure" is intended to mean a product substantially free of natural impurities that might interfere with the intended use of the compounds or make them unsuitable for the intended use.

It will be readily apparent to those skilled in the art that a number of modifications or changes may be made without departing from the spirit and scope of the present invention. Therefore, the invention is only to be limited by the claims.

We claim:

1. A phospholipid ester selected from the group consisting of the phospholipid esters of 9,11-octadecadienoic acid and the phospholipid esters of 10,12-octadecadienoic acid.

* * * * *